United States Patent

Galiana et al.

[11] Patent Number: 6,089,714
[45] Date of Patent: Jul. 18, 2000

[54] AUTOMATIC SEGMENTATION OF NYSTAGMUS OR OTHER COMPLEX CURVES

[75] Inventors: Henrietta L. Galiana, St. Lambert; Heather L. Smith, Montreal West, both of Canada

[73] Assignee: McGill University, Montreal, Canada

[21] Appl. No.: 09/251,144

[22] Filed: Feb. 17, 1999

Related U.S. Application Data

[60] Provisional application No. 60/075,096, Feb. 18, 1998.

[51] Int. Cl.[7] .................................................. A61B 3/08
[52] U.S. Cl. ........................................................ 351/202
[58] Field of Search ..................................... 351/200, 202; 706/16, 15, 14; 704/229, 226; 370/474

[56] References Cited

U.S. PATENT DOCUMENTS

| | | | |
|---|---|---|---|
| 5,745,382 | 4/1998 | Vilim et al. | 364/551.01 |
| 5,956,674 | 9/1999 | Smyth et al. | 704/229 |
| 5,991,308 | 11/1999 | Fuhrmann et al. | 370/474 |

OTHER PUBLICATIONS

"Parametric Classification of Segments in Ocular Nystagmus" by Claudio G. Rey and Henrietta L. Galiana, IEEE Transactions on Biomedical Engineering, vol. 38, No. 2, Feb. 1991, pp. 142–148.

*Primary Examiner*—George Manuel
*Attorney, Agent, or Firm*—Swabey Ogilvy Renault

[57] ABSTRACT

For segmenting a sampled signal having at least two temporally separate interleaved dominant components for the purposes of extracting one or more of the separate components, an automated method of analyzing the sampled signal is used. By selecting a model for the signal and a processing window dimension, a variance between the signal and a model value for the signal is measured within the window over the sampled domain to obtain a noise indicator value. A corner geometry value for the sampled signal is calculated within the same window over the domain. A transition indicator value is generated based on a ratio of the corner geometry value and the model value. The segmentation points are identified based on the transition indicator value and at least one of the noise indicator value and the model value within the window over the domain.

14 Claims, 5 Drawing Sheets

AUTOMATIC SEGMENTATION OF NYSTAGMUS OR OTHER COMPLEX CURVES

This application claims priority under 35USC§119(e) of U.S. Pat. application Ser. No. 60/075,096 filed Feb. 18, 1998.

FIELD OF THE INVENTION

The present invention relates to a method and apparatus for automatic identification of segments of signals having at least two temporally separate interleaved dominant components. Examples of such signals are ocular nystagmus, and Raman spectra having a fluorescence background signal.

BACKGROUND OF THE INVENTION

Eye movements triggered by any sensory stimulus or mental effort are reflex-like. They always consist of 2 intermingled components of variable length: so-called 'slow' phases, during which the eye trajectories correct for target or head displacement (visual pursuit, vestibulo-ocular reflex), and fast phases when the eyes saccade to new orbital positions. As a result, typical eye movements have a saw-tooth-like pattern called ocular nystagmus. The type of nystagmus is named after the associated sensory stimulus (e.g. vestibulo-ocular -VOR, optokinetic-OKN, pursuit-PN. . . ).

In the clinical or neurophysiological study of ocular reflexes, it is therefore necessary to first process the eye trajectories to flag and pool the desired 'slow' or 'fast' response segments. Reflex characterization and parameter estimation can only follow after this first stage of processing. Hence a general-purpose classifier, applicable to any nystagmus and all stimulus patterns is highly desirable.

In the context of eye movements, current classifiers are heavily dependent on human intervention, and are restricted in the range of their application. Most are in-house research tools for a specific application. Typically they either

- assume a priori the waveform of the slow-phase segments; as a result it is difficult to apply them in non-linear cases which are typical in clinical patients; or with different stimulus profiles without reprogramming.
- use simple eye velocity and/or interval duration criteria to classify segments; hence, are difficult to use at high fast phase rates, and high-amplitude stimulus levels.
- or use bandwidth-style criteria to filter out the high-frequency fast phases (this is the approach also used in Raman spectral analysis to remove fluorescence background), which distorts the estimated slow-phase profiles.

The results are highly unsatisfactory, and usually require intensive human viewing and editing. Hence they do not lend themselves to fully automated or real-time applications. Even more recent efforts using fuzzy logic or neural networks to detect patterns are also very limited in their application.

Work has been done on an automated and generalized approach for the classification of eye-movement segments, as published in the paper co-authored by one of Applicants, "Parametric Classification of Segments in Ocular Nystagmus", Claudio Rey and Henrietta Galiana, IEEE Transactions on Biomedical Engineering, Vol. 38, No. 2, Feb. 1991, the content of which is hereby incorporated by reference. This initial work was restricted to the study of the VOR, and often required human intervention to correct for classification errors due to non-linearities or dynamics in the input/output nystagmus process. Also the algorithm usually failed at high nystagmus rates, due to the nature of its filtered indicators, and was restricted to pure gain (scalar) representations in the VOR.

To Applicants' knowledge, an accurate and reliable method for automatic identification of segments of signals having at least two temporally separate interleaved dominant components is not known in the art of signal processing. Such a method would be useful not only in the biomedical application of analyzing nystagmus signals, but also in analyzing many other similar signals, such as Raman spectra signals having a fluorescence background signal.

SUMMARY OF THE INVENTION

It is an object of the invention to provide an algorithm which solves these previous restrictions, and can classify all types of eye movements with little or no human intervention.

According to a broad aspect of the invention, there is provided a method of identifying segmentation points in a sample signal having at least two separate interleaved dominant components for the purposes of extracting at least one of the separate components. The method comprises; selecting a model for one of the components in the signal and a data window dimension; measuring a variance between the signal and a model value for the one of the components in the signal within the window over a data stream to obtain a noise indicator value; calculating a corner geometry value for the one of the components in the signal within the window over the data stream and generating a transition indicator value based on a function of the corner geometry value and the model value; and determining the segmentation points for the one of the component based on the transition indicator value and at least one of the noise indicator value and the model value within the window over the data stream.

According to a further broad aspect of the invention, there is provided an apparatus for processing a sample signal having at least two separate interleaved dominant components and identifying segmentation points in the sample signal for the purposes of extracting at least one of the separate components. The apparatus comprises; means for measuring a variance between the signal and a model value for the one of the components in the signal within a predetermined window over a data stream to obtain a noise indicator value; means for calculating a corner geometry value for the one of the components in the signal within the window over the data stream and generating a transition indicator value based on a function of the corner geometry value and the model value; and means for generating values representing the segmentation points for the one of the component based on the transition indicator value and at least one of the noise indicator value and the model value within the window over the data stream.

Preferably, the step of determining is based on both the noise indicator value and the model value. In one preferred embodiment, the signal is an ocular nystagmus signal and the model is a linear model. The model may alternatively be a spontaneous model, and the step of selecting a model includes providing pseudo-input for stimulus. The model may also be a dynamic non-linear model, and the step of selecting a model includes providing filtered recorded input for stimulus.

Preferably, the corner geometry value is a bent-line value, and the transition indicator function is a ratio.

BRIEF DESCRIPTION OF THE DRAWINGS

The invention will be better understood by way of the following detailed description of a preferred embodiment, with reference to the appended drawings, in which.

DETAILED DESCRIPTION OF THE PREFERRED EMBODIMENT AND OTHER EMBODIMENTS

In the preferred embodiment, the invention is applied to analyzing ocular nystagmus signals. With reference to the flow chart of FIG. 1, those aspects of the classification process which were described in the above mentioned 1991 Rey and Galiana paper have been shaded. The additional novel aspects are left as white-background boxes. As can be seen, there are really 3 major steps to allow robust automatic classification of an eye movement trajectory:

i) Definition of an adequate though reduced model which approximates the expected input/output relationship (e.g. eye velocity vs. head velocity, or vs. target velocity etc.)

ii) Calculation of indicators based on this model, which describe the estimated parameters of the model (model indicator(s) MI), the quality of the fit (noise indicator NI), and the relative improvement in fit between the proposed model and a 'corner' convolution window (this confirms transition corners between slow and fast phases in indicator TI).

iii) Thresholds are applied to the three indicators to create a 'decision flag', which points to all data points compatible with the proposed 'model'. To be classified as slow-phase, a candidate segment must satisfy all three of the following: have an acceptable range on estimated model parameters, good quality of the fit given current noise conditions (low noise indicator), and lie between points of high likelihood for transitions (peaks in transition indicator).

The indicators are calculated inside a moving-time window. The window width is the same for all indicators: this width determines the maximally discriminated fast phase rate and sets the floor on the noise indicators during slow-phases. Another window variable is also available to the user if he/she wishes to further restrict the selection process to slow-phase segments of a minimal duration. Most parameters in the process have default values, but the user can change them to suit his needs in the calling sequences, for example widen the windows in high noise conditions. The algorithm is tuned such that the probability of accepting non-slow-phase data is near zero, sometimes at the cost of dropping valid slow-phase segments. This is preferred so that subsequent use of the marked data will provide slow-phase dynamics uncorrupted by artifacts (e.g. blinks or saccades).

An additional pass through the classification process can be applied if the user so wishes after viewing first-pass results (or the second pass can be eliminated up front, given a priori knowledge). If the profile of slow-phase segments selected in the first pass exhibits a significant non-linearity (NL) and phase shift (dynamics) with respect to the stimulus and a second pass is enabled, the estimated phase and NL are passed back to step i) to pre-filter the input stimulus sequence. This allows the use of tighter thresholds and more robust classification in the second pass.

Figure 2A:
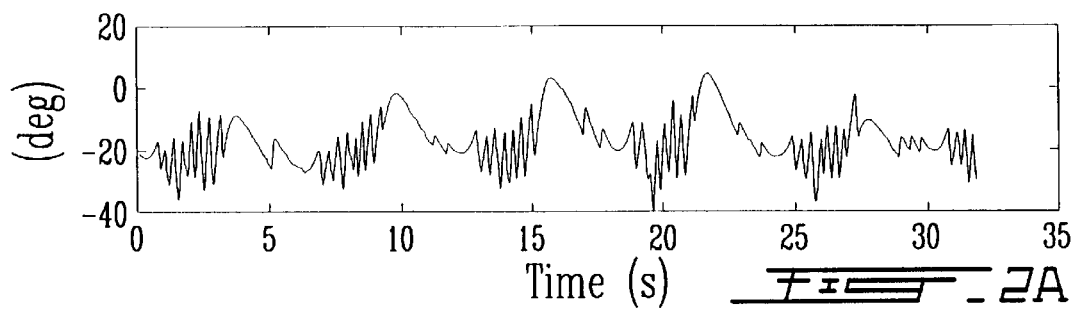
FIGS. 2a, 2b, 2c, 2d, and 2e are graphs of sample eye position, head position eye velocity, head velocity and slow-phase eye velocity, respectively, versus time for illustrating a nystagmus signal according to the preferred embodiment.
Figure 2B:
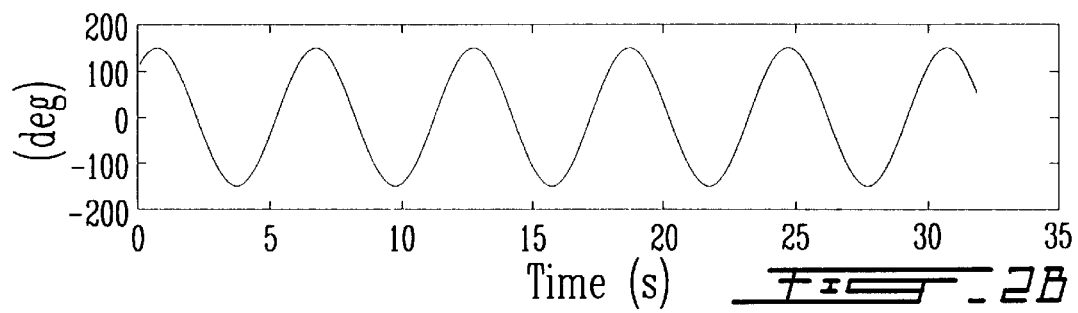
Figure 2C:
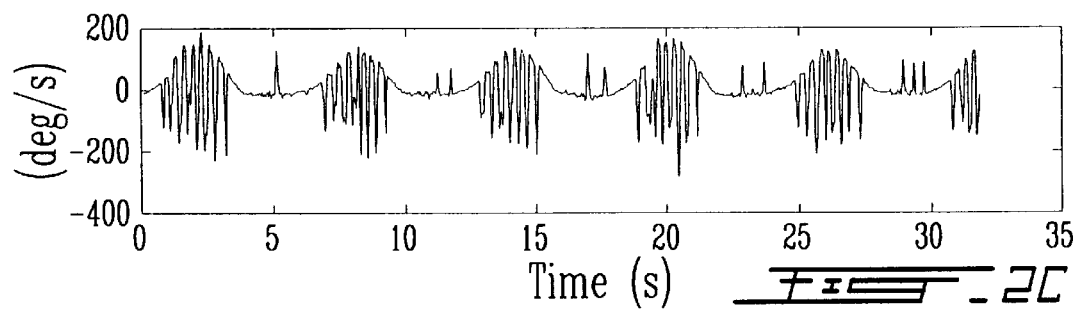
Figure 2D:
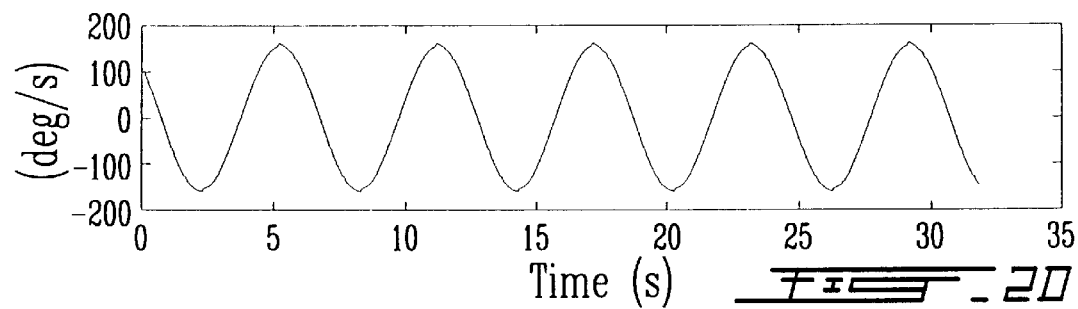
Figure 2E:
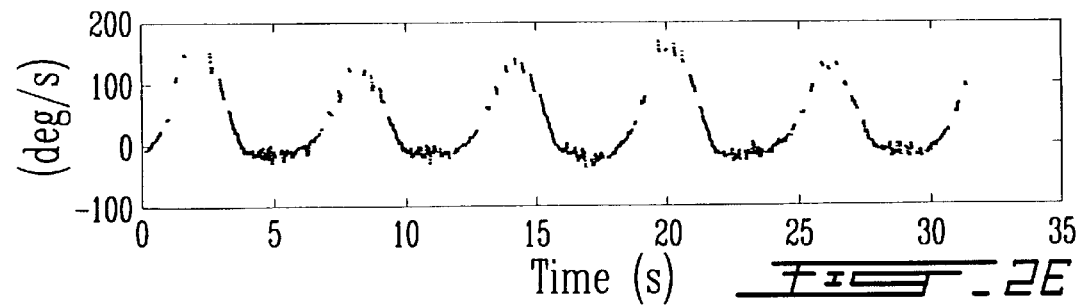

The result is a vector of indices pointing to the desired segments of the nystagmus record (usually slow-phases). An example of the resulting flagged slow-phase data is provided in FIG. 2e for a clearly non-linear case, after only the initial pass. The classification process can be inverted: i.e. tuned to point instead to saccadic (fast-phase) segments if the user wishes to study these types of eye movements.

Thus, the method can be adjusted for automatic segment classification, and can be applied to:

variable noise conditions any desired protocol with varying stimulus time profiles any reflex context (simply select appropriate model form for input/output pair)

The algorithm is provided with 2 data vectors which represent the input (X) and output (Y) stream of interest of length N samples, acquired at equal time intervals.

Typically, in the preferred embodiment, this data vector pair would represent the experimentally recorded eye and head velocities (EV=Y, HV=X in schematic above). However, this can change with the protocol at hand: e.g. use eye velocity and target velocity in the case of pure pursuit, head-fixed, etc. The procedure consists of the following sequence:

Postulate a Reduced Model Likely to Describe the Relationship Between Input and Output:

a) First a model is postulated to represent the data pair to allow subsequent fit by regression. In the mentioned 1991 Rey and Galiana paper, this was restricted to a simple algebraic relationship so that, $$Y_j = a\, X_j + n_j;$$

for every time sample "j"0 in the data vectors, and where $n_j$ is assumed to be a white noise sequence. In the generalized algorithm here, the postulated model can be more extensive and include dynamics and/or non-linearities in the descriptive equation. One descriptive form for nonlinear systems in discrete time is the Non-linear Auto-Regressive Moving-Average eXogenous-input formulation (NARMAX). An example for a first-order pole and quadratic non-linearity with bias is:

$$Y_j = m\, Y_{j-1} + a\, X_j + b\, X_j^2 + c + n_j$$

Figure 1:
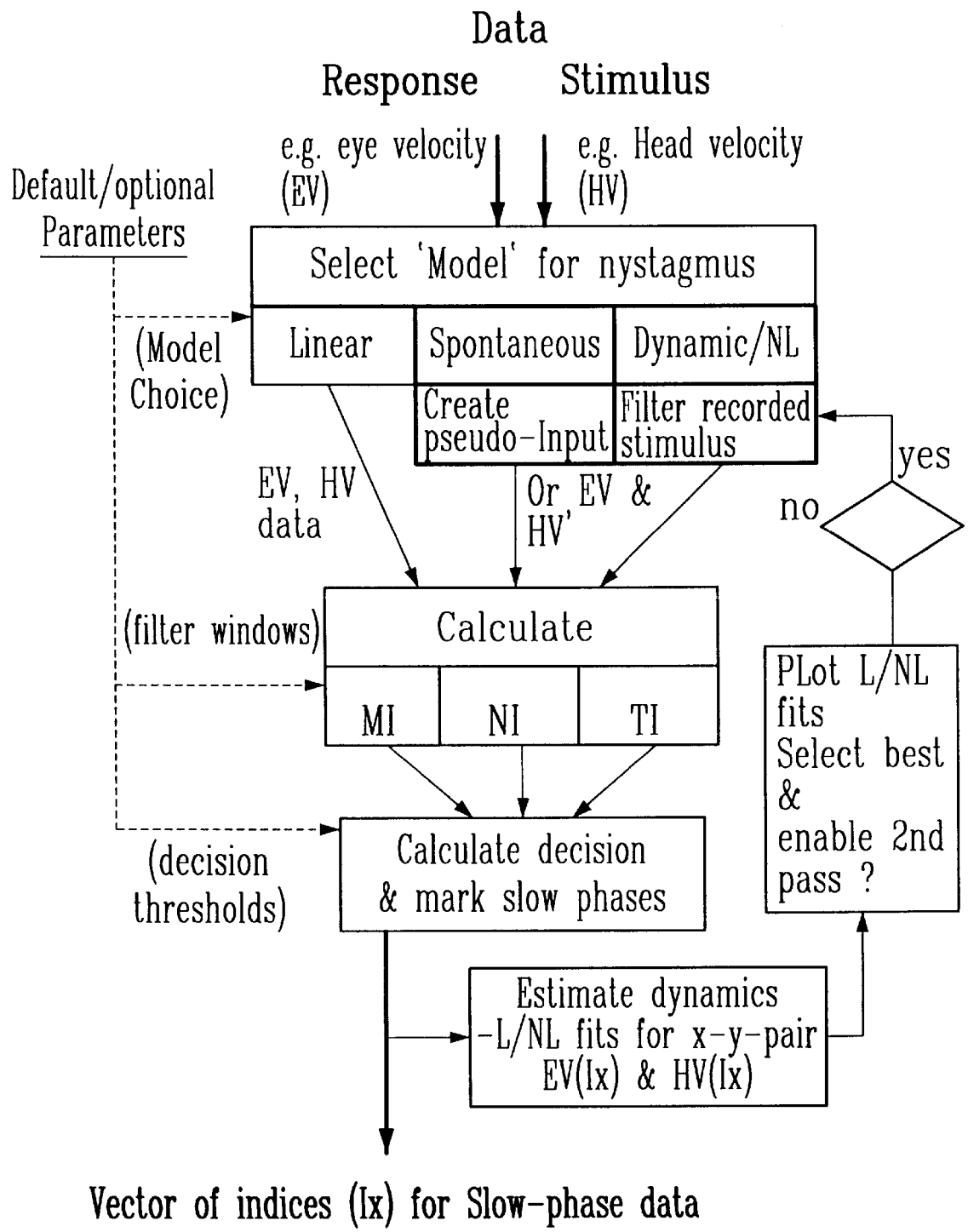
FIG. 1 is a flow chart of the method according to the preferred embodiment.

If there is a priori knowledge of the form of a non-linearity, it can be applied to X first, producing a filtered X' (HV' in FIG. 1). As a result, the model reduces to the simpler linear Auto-Regressive Moving-Average case (ARMA) with respect to X':

$$Y_j = m\, Y_{j-1} + a\, X_j + n_j$$

Otherwise, a first pass through the algorithm may provide an estimate of the non-linearity.

b) In some cases only the response (output) is available, so that a 'pseudo-input' is provided to appropriately drive the algorithm. Examples here are spontaneous nystagmus which causes eye movements in patients without measurable head movement, or caloric nystagmus caused by hot/cold water irrigation of the ear canal and thermal transmission through bone. Here it is usually sufficient to generate a vector of constant values, starting at the time of the initial response (step), and use this as the presumed vector representing the input, Y.

Calculate the Indicators:

a) The model indicators (MI) - First, classical regression is applied to obtain estimates for the coefficients in the above selected model(s). This procedure allows for time-varying coefficients, in order to detect changes used for classification. Hence, to find coefficient estimates at time sample 'k', the regression is applied only to windowed data of temporal width W samples, centered at 'k': i.e. data used is X'k−w/2 →X'k+w/2 with Y k+w/2 →Y k+w/2. This windowed regression is passed over the whole time sequence to produce vectors of coefficient estimates denoted by placing a 'θ' over the coefficient symbol (e.g. $\ddot{m}$, $\ddot{a}$, for 'm' and 'a' in the equations above). The resulting vectors of estimated coefficients are of length equal to that of the original data stream, less W samples. One or all of these estimated parameters can be used as part of the MI. These then provide an estimate of the expected model response, using the assumed representation, e.g.

Figure 3A:
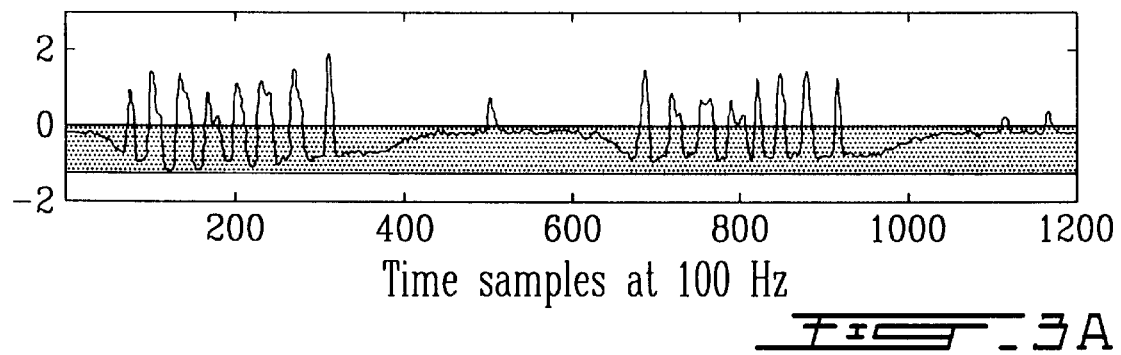
FIG. 3a, 3b and 3c are graphs of sample profiles for computed indicators and their thresholds for MI, NI and TI, respectively, according to the preferred embodiment.

$\ddot{Y}_j = \ddot{m}_j \ddot{Y}_{j-1} + \ddot{a}_j X'_j$, for the last model equation above, j=1, . . . N−W FIG. 3a provides a plot of the time variation of such a model coefficient (here $\ddot{a}$), for the data in FIG. 2a to FIG. 2e and a simple scalar model.

b) The noise indicator (NI) - The NI represents the root-mean-squared estimates of the residuals obtained over the window width at each time sample. It is a measure of the quality of the fit, obtained by taking the difference between observed responses and those predicted by the model, at each step in time viewed through window of width W. Hence, at any given time instant "j".

$$NI_j = rms_j = \sqrt{\frac{1}{W} \sum_{r=-W/2}^{r=W/2} (Y_{j+r} - \hat{Y}_{j+r})^2}$$

Figure 3B:
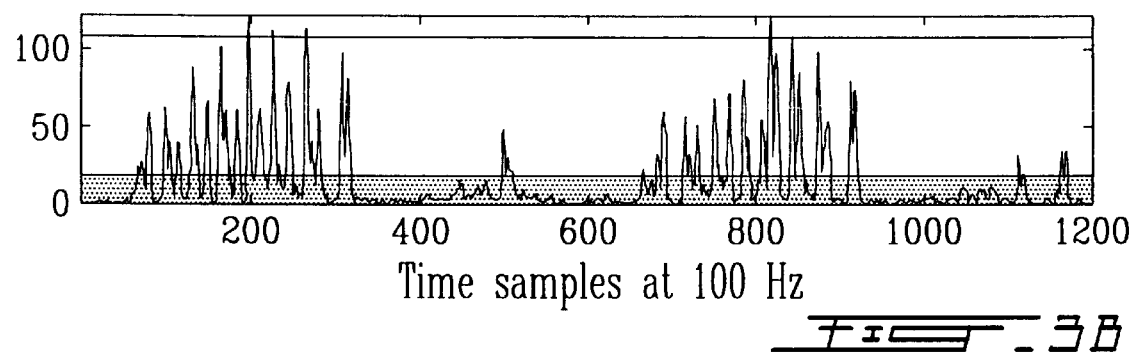

Again, in FIG. 3b, you can find the time variation of the NI for the data in FIG. 1a to FIG. 2e.

c) The transition indicator (TI) - The TI consists of the ratio of two NI indicators, obtained from two alternate model fits in a same window of width W. The first NI is that computed in b) using the postulated model equation over W samples. In the 1991 Rey and Galiana paper, the second NI repeated the procedures of a) and b), but within a shortened window W/2 to allow higher bandwidth.

Figure 4:
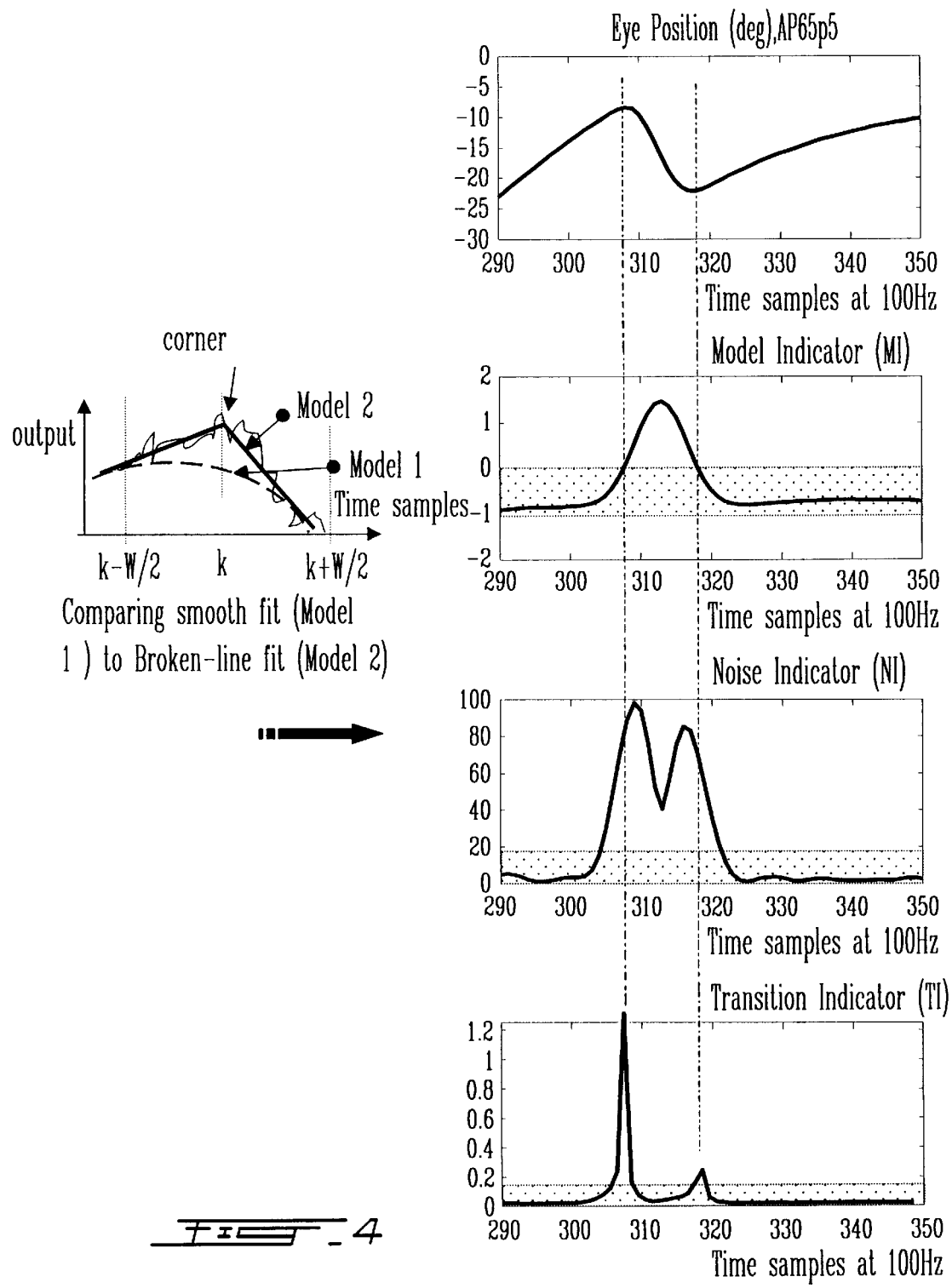
FIG. 4 is a graph illustrating the method of fitting a "broken line" and a curve to the nystagmus signal according to the preferred embodiment.

According to the invention, this approach is replaced with an NI (NIC) computed instead by applying a descriptive model which best describes the shape of the response trajectory at the moment of a transition from fast-to-slow or slow-to-fast segment intervals. That is, NIC is computed according to the equation in b), but this time after fitting a 'corner geometry' to the eye trajectory which is modeled by two straight lines each of width W/2 and constrained to meet at a common point in the center of the window (see FIG. 4). Such a segmented line fit can easily be derived by standard regression derivations. In summary, the model described in a) and b) proposes a smooth dynamic representation fitted over W samples, while the broken line model in FIG. 4 fitted over the same W data point pairs is best suited for the exact points of transition (corners in data curve). Between transitions the two models are equivalent in their goodness of fit. Hence the ratio of the two NIs from these two fits will produce large values at each transition point, and much lower values near one elsewhere.

$$TI_j = \frac{NI_j}{NIC_j}$$

Figure 3C:
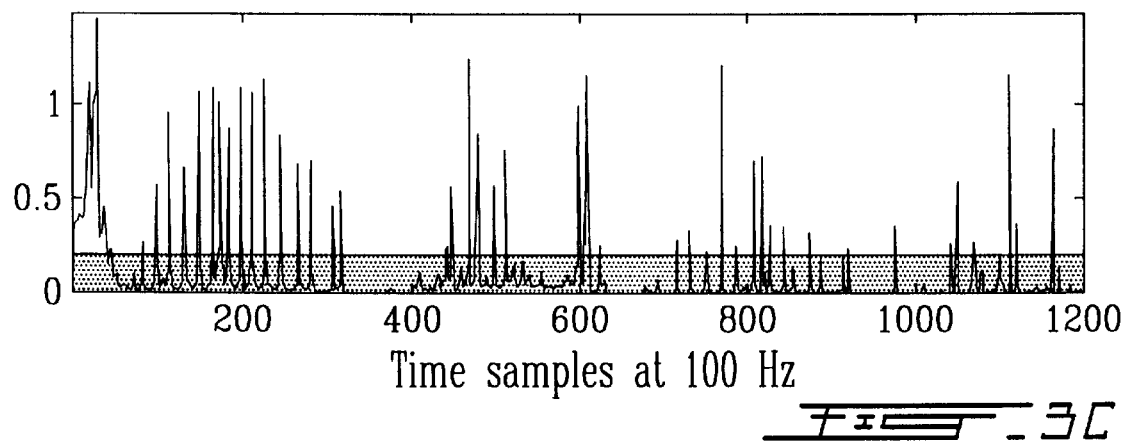

See FIG. 3c for an example of time variations in TI and its large peaks at nystagmus corners. A zoomed in version is provided in the right panel of FIG. 4. This approach to calculating the TI is much more robust than the prior art. It provides strong marker peaks above the background level, even at high fast phase rates.

Applying Logical Thresholds to Indicators to Define a Classification Flag

The setting of decision thresholds to select intervals of slow phases is now described. The procedure is easily adapted to select instead fast phases or saccades by reversing the logic. A decision flag is computed at each time interval based on the concurrent values of all three (or more) indicators. Referring to FIG. 3a, an acceptable range (max/min) is applied to MI, a minimum value above background noise is set for NI (slow phases should lie below it), and generally a high threshold is set for TI to pass only large peaks marking nystagmus corners. If all three indicators at sample 'k' simultaneously satisfy the set conditions, then the time index 'k' is stored as an acceptable index in the final flag vector (lx, schema). At this point, classification is completely based on local information, and could be executed in real time with a processing lag of W/2 samples.

Additionally, the acceptable slow-phase intervals can be expanded outward towards the corners demarked by impulses on TI. This provides more accurate pinpointing of the beginning and end of slow-phase segments. However it would require off-line processing, or an additional processing delay for real-time processing, equal to the effective filtering bandwidth of a window width 'W'. The advantage of our signal 'modeling' approach for classification is that it can rely on local parameters, rather than a global fit over the whole record duration (typical of previous methods). Hence it requires a minimum of a priori assumptions on the nature of the relationship between input and output. The result is simply a vector of indices pointing to the raw data sample pairs which satisfy the conditions for selection. A full study of true dynamics or non-linear behaviour between input and output can then be applied separately.

Special Considerations and Guidelines of Operation

Classification according to the preferred embodiment requires very little (if any) human intervention, and is very tolerant of approximations in the model used for detection. It can detect any segment mode changes observable outside the background noise levels by the human eye: usually this means that all slow-phase segments will be accurately classified if the regression window (reducing noise) is no larger than the duration of the shortest slow phase interval. Hence there is a tradeoff between reducing noise in the model estimates (noise indicators) and the range of nystagmus rates to be processed. If a narrow window is imposed by high rates of slow/fast intervals, then the thresholds on the noise indicator can be raised above the slow-phase floor to compensate.

The improved transition indicator (TI) calculates the ratio of noise indicators for the proposed model (numerator) and a simple 'broken line' model (denominator), Since a broken line describes very well the trajectory of an eye movement during transition from slow to fast phases (or vice versa), it will produce very low residual errors when the window is centered on a transition corner. Hence the transition indicator now produces huge narrow peaks at the beginning and end of any fast phase, which are easily distinguished from near-one levels during slow phases, or in the middle of long fast phases. This information is used to advantage with the other indicators to allow accurate classification at high fast phase rates.

An example of the indicator profiles and their decision thresholds is provided in FIG. 3, which corresponds to the classified data in FIG. 2a to FIG. 2e.

The model indicator (MI) corresponds to the estimated parameter in the model regression: its thresholds are placed to include the expected parameter range during slow phases only. In the case of a linear scalar model but actually non-linear reflex, the MI will have a broad acceptable range during slow phases. On the other hand if the stimulus is preprocessed ($2^{nd}$ pass) with an estimated non-linearity (and possibly dynamics), the resulting MI will be nearly constant for all slow-phase segments and allow tight thresholds.

The noise indicator (NI) represents the rms of the model in the moving time window. The lower threshold puts an upper limit on the NI for accepted slow-phases, the upper threshold can be used to detect artifacts. Acceptable fast phases or saccades will have NI indicators between these two thresholds. The lower NI threshold denotes regions where the data can be described by the proposed slow-phase model in a statistical sense. The wider the window in calculating indicators, the better (lower) will be the NI floor, but at the cost of time resolution.

The transition indicator (TI) is used to recover acceptable slow-phase data points from the original slow-phase data (unfiltered) by expanding the slow-phase indices 'outwards' in a segment until the TI exceeds a threshold (remember TI peaks mark location of a transition). Hence, despite the need to filter data in the calculation of indicators, the precision of segment location can be preserved as in the original raw data. Other methods of classification based purely on filtering approaches always lose slow-phase data near transitions.

Clearly, the key to optimal results for reliable classification lies in the accuracy of the proposed model, since this allows tighter indicator thresholds. The following guidelines are suggested:

I. With no a priori knowledge, use the scalar model which assumes linear gain between stimulus and response if the input is a pure sine wave. The default value −0.7 is valid for VOR in the dark; this should be changed to a positive scalar (~1) for visual reflexes. This approach will work for almost any VOR nystagmus stimulated at frequencies above about 0.02 Hz and for visual reflexes below about 0.5 Hz. Otherwise a dynamic model must be used.

II. For spontaneous nystagmus or gaze shifts, or caloric nystagmus (where no measured input exists), a pseudo-stimulus must be generated to allow comparison in the algorithm with the eye response. This normally simply involves postulating a small D.C. level, and the algorithm basically acts on the NI and MI indicators (see above).

III. For any cases where dynamics are expected (such as for broad-band inputs), the best classification will occur if the stimulus is pre-filtered by suitable dynamics before combining with eye responses in the algorithm. This means using high-pass canal dynamics (~5s–7s time constant) for low-frequency and D.C. VOR, or low-pass visual dynamics (~⅙ s time constant) for visual reflexes.

The algorithm automatically takes care of suitable stimulus pre-processing in the model selection stage, once the user chooses one of the three options.

Other Applications of the Present Invention

Figure 5A:
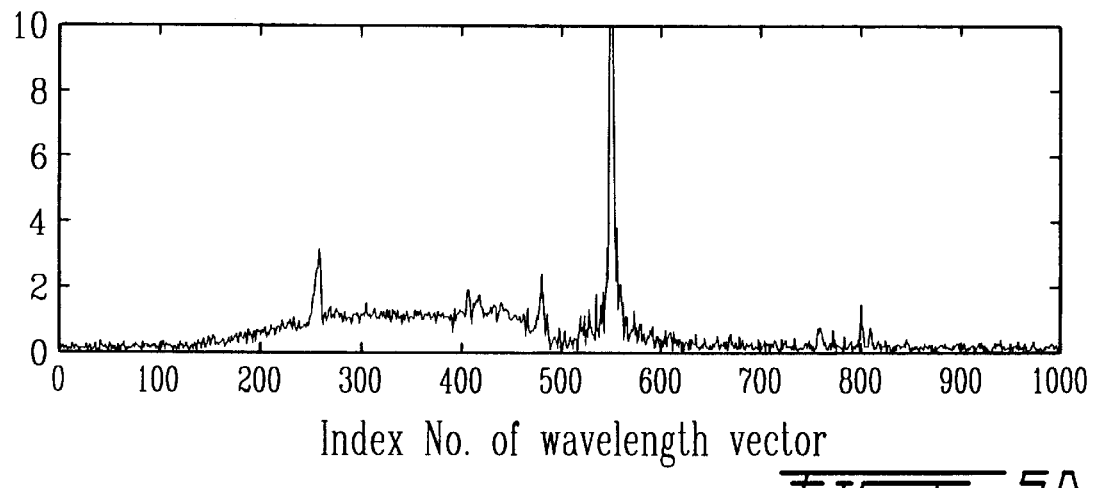
FIGS. 5a and 5b illustrate an original normalized spectrum and a normalized Raman spectrum representing a Raman spectrum signal having both Raman effect and fluorescence signal segments identified for automated analysis according to an alternative embodiment of the invention.
Figure 5B:
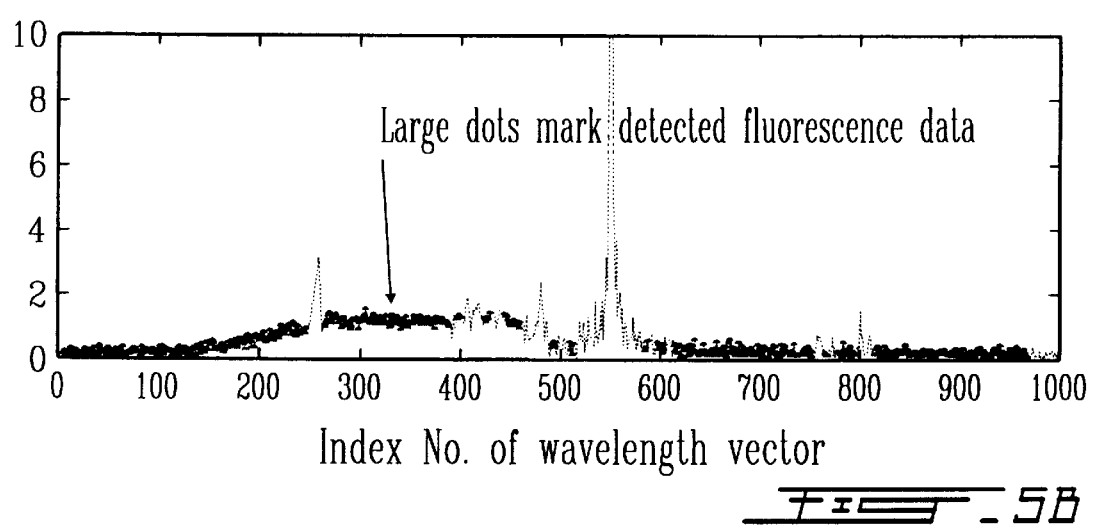

The problem of signal segmentation can be present in several quite diverse contexts. For example, sorting true Raman peaks from slow background fluorescence is a problem in Raman spectrometry. A method that can accomplish this would remove a source of noise in Raman analysis and facilitate the task of spectra identification for element detection. The algorithm can accomplish this simply by postulating an appropriate 'model' for the expected fluorescence background, akin to the pseudo step inputs used for caloric nystagmus. An example is provided in FIG. 5a and FIG. 5b.

Generally, the method according to the invention can be extended to sorting of all types of eye movements or complex trajectories into two expected modes. Adapting the classification only requires adjusting the 'model' in the regression stage to represent the function of the current input/output pair during the mode of interest. Models used in the generation of indicators can be as complex as desired if particular dynamics or non-linearities are needed.

Thresholds and markers can be adapted to reverse the classification procedure, and instead detect or mark fast-phase segments (saccades or $2^{nd}$ complement mode)

Since eye movements can be auto-classified, the algorithm could be used as an event detector inside a more complex human-machine interface, for example as an aid in eye-driven control (handicapped applications, head-free applications). In this case gaze (eye+head) is expected to better serve as the reference signal for classification. The classifier can then be tuned to the properties of the intended human operator for full automation in real time (see below).

Since classification is done based on local information in a small window, the algorithm could be ported in dedicated digital or analog hardware for real-time, on-line processing. Processing delay would only be the length (time aperture) of the indicator filters. Currently this is set to about 7–11 samples at a 100 Hz data rate (i.e. 70–110 ms).

Although the invention has been described in this specification With reference to a preferred embodiment and other specific embodiments, it is to be understood that these embodiments have been described in detail for the purposes of teaching the present invention only, and not to limit the breadth of the scope of the invention as defined in the appended claims.

What is claimed is:

1. A method of identifying segmentation points in a sample signal having at least two separate interleaved dominant components for the purposes of extracting at least one of said separate components, said method comprising:

selecting a model for one of said components in said signal and a data window dimension;

measuring a variance between said signal and a model value for said one of said components in said signal within said window over a data stream to obtain a noise indicator value;

calculating a corner geometry value for said one of said components in said signal within said window over the data stream and generating a transition indicator value based on a function of said corner geometry value and said model value; and determining said segmentation points for said one of said component based on said transition indicator value and at least one of said noise indicator value and said model value within said window over the data stream.

2. The method as claimed in claim 1, wherein said step of determining is based on both said noise indicator value and said model value.

3. The method as claimed in claim 2, wherein said signal is an ocular nystagmus signal and said model is a linear model.

4. The method as claimed in claim 2, wherein said signal is an ocular nystagmus signal and said model is a spontaneous model, said step of selecting a model including providing pseudo-input for stimulus.

5. The method as claimed in claim 2, wherein said signal is an ocular nystagmus signal and said model is a dynamic non-linear model, said step of selecting a model including providing filtered recorded input for stimulus.

6. The method as claimed in claim 2, wherein said corner geometry value is a bent-line value, and said function is a ratio.

7. The method as claimed in claim 1, wherein said signal is an ocular nystagmus signal and said model is a linear model.

8. The method as claimed in claim 7, wherein said corner geometry value is a bent-line value, and said function is a ratio.

9. The method as claimed in claim 1, wherein said signal is an ocular nystagmus signal and said model is a spontaneous model, said step of selecting a model including providing pseudo-input for stimulus.

10. The method as claimed in claim 9, wherein said corner geometry value is a bent-line value, and said function is a ratio.

11. The method as claimed in claim 1, wherein said signal is an ocular nystagmus signal and said model is a dynamic non-linear model, said step of selecting a model including providing filtered recorded input for stimulus.

12. The method as claimed in claim 11, wherein said corner geometry value is a bent-line value, and said function is a ratio.

13. The method as claimed in claim 1, wherein said corner geometry value is a bent-line value, and said function is a ratio.

14. An apparatus for processing a sample signal having at least two separate interleaved dominant components and identifying segmentation points in the sample signal for the purposes of extracting at least one of said separate components, said apparatus comprising:

means for measuring a variance between said signal and a model value for said one of said components in said signal within a predetermined window over a data stream to obtain a noise indicator value;

means for calculating a corner geometry value for said one of said components in said signal within said window over the data stream and generating a transition indicator value based on a function of said corner geometry value and said model value; and means for generating values representing said segmentation points for said one of said component based on said transition indicator value and at least one of said noise indicator value and said model value within said window over the data stream.

* * * * *